United States Patent
Sadaba Zubiri et al.

(10) Patent No.: US 10,189,778 B2
(45) Date of Patent: Jan. 29, 2019

(54) PROCESS FOR THE PREPARATION OF METHIONINE ALPHA-HYDROXY ANALOGUES FROM SUGARS AND DERIVATIVES THEREOF

(71) Applicant: HALDOR TOPSØE A/S, Kgs. Lyngby (DK)

(72) Inventors: Irantzu Sadaba Zubiri, Frederiksberg (DK); Esben Taarning, Frederiksberg (DK); Despina Tzoulaki, Copenhagen (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/568,943

(22) PCT Filed: Apr. 29, 2016

(86) PCT No.: PCT/EP2016/059661
§ 371 (c)(1),
(2) Date: Oct. 24, 2017

(87) PCT Pub. No.: WO2016/174231
PCT Pub. Date: Nov. 3, 2016

(65) Prior Publication Data
US 2018/0118673 A1 May 3, 2018

(30) Foreign Application Priority Data

Apr. 30, 2015 (DK) .................. 2015 00265

(51) Int. Cl.
| | |
|---|---|
| *A23K 20/10* | (2016.01) |
| *A23L 33/17* | (2016.01) |
| *A23K 20/142* | (2016.01) |
| *C07C 319/14* | (2006.01) |
| *C07C 321/04* | (2006.01) |
| *C07C 323/52* | (2006.01) |

(52) U.S. Cl.
CPC .......... *C07C 319/14* (2013.01); *A23K 20/142* (2016.05); *A23L 33/17* (2016.08); *C07C 321/04* (2013.01); *A23K 20/10* (2016.05); *A23V 2002/00* (2013.01)

(58) Field of Classification Search
CPC ....... A23K 20/142; A23K 20/10; A23L 33/17; C07C 319/14; C07C 321/04; A23V 2002/00
See application file for complete search history.

(56) References Cited

U.S. PATENT DOCUMENTS

| | | |
|---|---|---|
| 4,933,161 A | 6/1990 | Vaughan et al. |
| 7,094,932 B2 | 8/2006 | Majerski et al. |
| 7,402,705 B2 | 7/2008 | Redlingshofer et al. |
| 2006/0183945 A1 | 8/2006 | Redlingshofer et al. |
| 2010/0197965 A1 | 8/2010 | Belliere-Baca et al. |
| 2011/0229626 A1* | 9/2011 | Devaux ................. C07C 45/52 426/648 |

FOREIGN PATENT DOCUMENTS

| | | |
|---|---|---|
| EP | 2 184 270 A1 | 5/2010 |
| WO | WO 98/32735 A1 | 7/1998 |
| WO | WO 2015/024875 A1 | 2/2015 |
| WO | WO 2016/083137 A1 | 6/2016 |

OTHER PUBLICATIONS

M. Holm et al., "Conversion of Sugars to Latic Acid Derivatives Using Heterogeneous Zeotype Catalysts," Department of Chemistry, Technical University of Denmark, Lyngby, Denmark, vol. 328, Issue 5978, pp. 602-605, Apr. 30, 2010.
M. Dusselier et al., "Mechanistic Insight into the Conversion of Tetrose Sugars to Novel a Hydroxy Acid Platform Molecules," vol. 5. Issue 2, pp. 569-575, Nov. 30, 2012.
J.S. Roberts, "Thiols," Kirk-Othmer Encyclopedia of Chemical Technology, Philips Petroleum Company, CH&A Corporation, Dec. 4, 2000.

* cited by examiner

*Primary Examiner* — Pancham Bakshi
*Assistant Examiner* — Mark R Luderer
(74) *Attorney, Agent, or Firm* — Blank Rome LLP

(57) ABSTRACT

A process for the preparation of methionine a-hydroxy analogue and derivatives thereof comprising contacting one or more sugars or derivatives thereof with a metallo-silicate composition in the presence of a compound comprising sulphur and a solvent.

23 Claims, 1 Drawing Sheet

Figure 1:
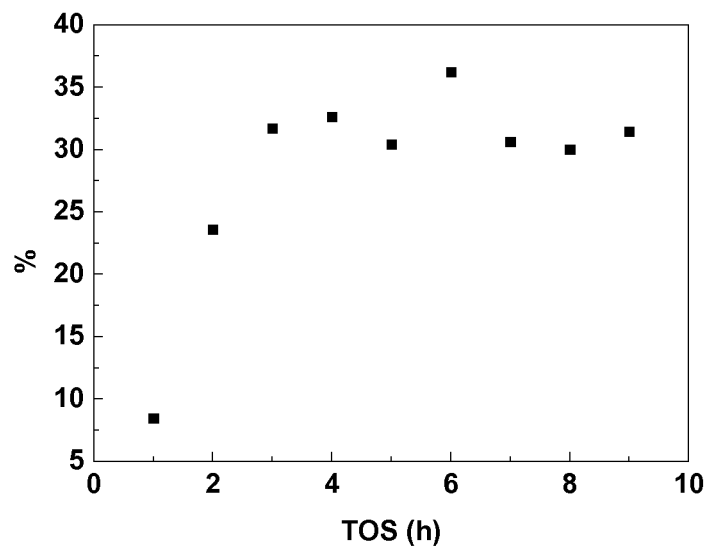

PROCESS FOR THE PREPARATION OF METHIONINE ALPHA-HYDROXY ANALOGUES FROM SUGARS AND DERIVATIVES THEREOF

A process for the preparation of methionine α-hydroxy analogue and derivatives thereof from sugars in the presence of zeotype compounds.

BACKGROUND

Carbohydrates represent the largest fraction of biomass and various strategies for their efficient use as a feedstock for the preparation of commercial chemicals are being established. Biomass is of particular interest due to its potential for supplementing, and ultimately replacing, petroleum as a feedstock for such purposes. Carbohydrates obtainable from biomass comprise C2 to C6 sugars and are of particular interest industrially as they are a potential source of highly functionalised short chain carbon compounds.

This invention is directed towards the preparation of methionine α-hydroxy analogue and derivatives thereof from sugars in the presence of zeotype compounds. Methionine α-hydroxy analogue is 2-hydroxy-4-(methylthio) butanoic acid. Methionine α-hydroxy analogue and derivatives thereof may be used as a food/nutritional supplement in animal feed compositions/formulations.

It is known that C2-C6 sugars may be converted to methyl lactate and methyl vinylglycolate (MVG) in the presence of zeo-type materials such as Sn-BEA. EP 2 184 270 B1 and Science (2010) 328, pp 602-605 report average yields of methyl lactate of 64%, 43% and 44% at 160° C., in the presence of Sn-BEA and methanol from sucrose, glucose and fructose, respectively. Methyl vinylglycolate (MVG) is the major by-product with a reported yield of 3-11%. MVG may be produced in yields of up to 56% from the C4 sugar D-erythrose.

WO 98/32735 discloses a process for the preparation of methionine α-hydroxy analogue methyl ester, 2-hydroxy-4-(methylthio) butanoic acid methyl ester, in an 85% yield via a free radical addition of methylthiol to a non-conjugated olefinic substrate, i.e. methyl vinylglycolate (MVG). Although high yielding, radical reactions have the potential to form region-isomeric by-products.

WO 98/32735 also discloses an alternative, multi-step, commercially feasible process for preparing methionine α-hydroxy analogue, 2-hydroxy-4-(methylthio)butanoic acid. The process comprises a Michael addition of methyl mercaptan to acrolein (a conjugated olefinic substrate) in the presence of an organic amine catalyst to produce 3-(methylthio)-propanal, followed by nitrile addition and hydrolysis to the acid. Although the process is industrially feasible, the use of toxic and expensive reagents such as HCN and acrolein should be avoided.

ChemCatChem (2013) 5, pp 569-575 discloses the conversion of tetroses (C4 sugars) to MVG and MMHB under homogenous catalytic conditions. MMHB is selectively produced from erythrulose (C4 sugar) in the presence of a homogenous tin chloride catalyst.

Accordingly, it is desirable to provide an alternative process for the preparation of methionine α-hydroxy analogue and derivatives thereof. In particular, it is desirable to provide a process that is industrially feasible, it is therefore desirable that the process is high yielding, direct and selective. It is desirable that the process is carried out under conditions that are industrially feasible, with regents or catalysts that enable ease of production and reduced toxic waste, such as the use of heterogenous catalysts that may be regenerated. Additionally, the provision of a process wherein the substrates are derived from renewable sources such as C2-C6 sugars, is desirable. In particular because the sugar substrates are much less toxic and much cheaper than, for example acrolein and the HCN reagent, consequently the use of sugar substrates significantly lowers the costs of production.

Disclosure of the Invention

It has surprisingly been found that a methionine α-hydroxy analogue and derivatives thereof is obtainable by contacting one or more sugars with a metallo-silicate composition in the presence of a compound comprising sulphur and a solvent.

The methionine α-hydroxy analogue and derivatives thereof may be represented by the formula

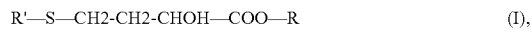

wherein R is selected from the group consisting of H, $C_1$-$C_8$ alkyl or alkaline or alkaline-earth metals; and R' is selected from the group consisting of H and methyl.

The methionine α-hydroxy analogue and derivatives thereof may alternatively be represented as follows:

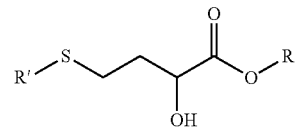

It has surprisingly been found that a high yield of the methionine α-hydroxy analogue and derivatives thereof is obtainable according to the process of the present invention.

The compound comprising sulphur is preferably a compound of the formula RSR', wherein R and R' are selected from the group consisting of H, C1-05 alkyl or alkaline or alkaline-earth metals. The compound comprising sulphur is preferably selected from the group consisting of $C_1$-$C_5$ alkyl thiol, $C_1$-$C_5$ alkyl thiol salts, dimethylmercaptan, dimethyl disulphide and hydrogen sulphide. $C_1$-$C_5$ alkyl thiol is in the present context meant to refer to mono-and di-substituted thiols with a substituent comprising a straight or branched chain saturated aliphatic alkyl group comprising one, two, three, four or five carbons. $C_1$-$C_5$ alkyl thiol is in the present context meant to refer to an alkyl thiol selected from the group consisting of methane thiol, ethane thiol, straight or branched chain propane thiol, straight or branched chain butane thiol and straight or branched chain pentane thiol.

$C_1$-$C_5$ alkyl thiol salt is in the present context meant to refer to the alkali or alkaline earth metal salt of a $C_1$-$C_5$ alkyl thiol. Specifically, $C_1$-$C_5$ alkyl thiol salt is in the present context meant to refer to a $C_1$-$C_5$ alkyl thiol in the salt form wherein the cation is selected from the group consisting of sodium, potassium, lithium, magnesium and calcium. Specifically, $C_1$-$C_5$ alkyl thiol salt is in the present context meant to refer to a $C_1$-$C_5$ alkyl thiol selected from one or more of the group consisting of $NaSCH_3$, $KSCH_3$, $Ca(SCH_3)_2$ and $Mg(SCH_3)_2$.

Hydrogen sulphide can be used as sulphur compound to produce 2-hydroxy-4-mercapto-butanoic acid or esters thereof, which can be further converted to the methionine α-hydroxy analogues by reaction with methanol. Alternatively, hydrogen sulphide can be used to form a $C_1$-$C_5$ alkyl thiol in the presence of the sugar, an alcohol and an acidic catalyst, as described in Roberts, J. S. 2000. Thiols, Kirk-Othmer Encyclopedia of Chemical Technology.

The methionine α-hydroxy analogue and derivatives thereof are selected from the group consisting of 2-hydroxy-4-($C_{1-5}$ alkylthio)butanoic acid, salts and esters thereof. $C_{1-5}$ alkylthio corresponds to the $C_{1-5}$ alkyl thio compound comprising sulphur present in the process. Preferably, the methionine α-hydroxy analogue and derivatives thereof are selected from the group consisting of 2-hydroxy-4-(methylthio)butanoic acid, salts and esters thereof. Preferably, the methionine α-hydroxy analogue and derivatives thereof are selected from the group consisting of 2-hydroxy-4-(methylthio)butanoic acid, alkali and alkaline earth metal salts and $C_{1-8}$ alkyl esters thereof. Preferably, the methionine α-hydroxy analogue and derivatives thereof are selected from the group consisting of 2-hydroxy-4-(methylthio)butanoic acid, alkali and alkaline earth metal salts and $C_{1-8}$ alkyl esters thereof.

$C_{1-8}$ alkyl esters is in the present context meant to refer to esters comprising the alkyl group selected from the group consisting of methyl, ethyl, propyl, butyl, isopropyl, isobutyl, pentyl, hexyl, heptyl, octyl and 2-ethylhexyl. Alkali and alkaline earth metal salts mean salts of the acid wherein the salt cation is selected from the group I and group II metals.

In one embodiment of the invention the methionine α-hydroxy analogue and derivatives thereof is 2-hydroxy-4-(methylthio)butanoic acid.

In a another embodiment of the invention the methionine α-hydroxy analogue and derivatives thereof is selected from the group consisting of 2-hydroxy-4-(methylthio)butanoic acid methyl ester, 2-hydroxy-4-(methylthio)butanoic acid ethyl ester, 2-hydroxy-4-(methylthio)butanoic acid propyl ester, 2-hydroxy-4-(methylthio)butanoic acid butyl ester, 2-hydroxy-4-(methylthio)butanoic acid isopropyl ester, 2-hydroxy-4-(methylthio)butanoic acid pentyl ester, 2-hydroxy-4-(methylthio)butanoic acid hexyl ester, 2-hydroxy-4-(methylthio)butanoic acid heptyl ester, 2-hydroxy-4-(methylthio)butanoic acid octyl ester and 2-hydroxy-4-(methylthio)butanoic acid 2-ethylhexyl ester.

The one or more sugars or derivatives thereof are selected from the group consisting of C2-C6 sugars or derivatives thereof. C2-C6 sugars or derivatives thereof is in the present context meant to refer to carbohydrates commonly found in biomass selected from the group consisting of glucose, fructose, galactose, mannose, sucrose, xylose, erythrose, erythrulose, threose, glycolaldehyde and 2-hydroxy-γ-butyrolactone. The one or more sugars or derivatives thereof may be used in solution or it may be a sugar syrup. Such a solution and syrup may be referred to as a sugar composition. The sugar composition may contain the solvent. Accordingly, the one or more sugars and derivatives thereof may be mixed with the solvent and/or the compound comprising sulphur. before it is contacted with the metallo-silicate composition. It may be referred to as a reaction mixture.

The process is preferably a one step process wherein the methionine α-hydroxy analogue and derivatives thereof are obtainable directly from the sugar substrate by contacting one or more sugars with a metallo-silicate composition in the presence of a compound comprising sulphur and a solvent.

In a further embodiment of the invention the sugars can be used in the presence of other $C_1$-$C_3$ oxygenates such as, acetol, pyruvaldehyde, formaldehyde and glyoxal. Glycolaldehyde (C2 sugar) can be produced together with minor amounts of other $C_1$-$C_3$ oxygenates by hydrous thermolysis of sugars according to the procedure described in U.S. Pat. No. 7,094,932 B2 and PCT/EP2014/053587.

The methionine α-hydroxy analogue and derivatives thereof are also obtainable by subjecting the one or more sugars or derivatives thereof to a pyrolysis step to obtain a pyrolysis product and subsequently contacting the pyrolysis product with the metallo-silicate composition in the presence of the compound comprising sulphur and the solvent.

Metallo-silicate composition refers to one or more solid materials comprising silicon oxide and metal and/or metal oxide components, wherein the metal and/or metal oxide components are incorporated into and/or grafted onto the surface of the silicon oxide structure (i.e. the silicon oxide structure comprises M-O—Si bonds). The silicon oxide structure is also known as a silicate. Metallo-silicate compositions may be crystalline or non-crystalline. Non-crystalline metallo-silicates include ordered mesoporous amorphous or other mesoporous amorphous forms. The metallo-silicate composition is selected from one or more of the group consisting of zeotype materials and ordered mesoporous amorphous silicates.

Preferably the active metal of the metal and/or metal oxide component is selected from one or more of the group consisting of Ge, Sn, Pb, Ti, Zr and Hf. The genus of zeotype materials encompasses the zeolite material genus. Preferably the zeotype material has a framework structure selected from the group consisting of BEA, MFI, FAU, MOR and FER. Preferably the ordered mesoporous amorphous silicate has a structure selected from the group consisting of MCM-41 and SBA-15. In a preferred embodiment, the metallo-silicate composition is a zeotype material. More preferably the metallo-silicate composition is a zeotype material and is selected from the group consisting of Sn-BEA, Sn-MFI, Sn-FAU, Sn-MCM-41 and Sn-SBA-15.

The solvent is preferably selected from one or more of the group consisting of methanol, ethanol, 1-propanol, 1-butanol, 2-propanol, 2-butanol, DMSO and water.

WO 2015/024875 discloses that in certain conditions, the presence of a metal ion in the reaction solution is beneficial to the yield. WO 2015/024875 provides experimental details describing the origin and addition of the metal ion to the process either via the catalyst itself or independently of the catalyst.

A further embodiment of the present invention is a basic reaction solution. The basic solution may be obtainable by the addition of one or more basic components. The basic component may be selected from one or more of the reagents selected from a metal salt and a basic polymer resin. Basic polymer resin may be for example a basic amberlyst resin.

The metal salt comprises a metal ion. Preferably the metal ion is selected from the group consisting of potassium, sodium, lithium, rubidium and caesium. Preferably the metal salt is a salt of an alkaline earth metal or alkali metal and anion is selected from the group consisting of carbonate, nitrate, acetate, lactate, chloride, bromide and hydroxide. Even more preferably the metal ion originates from one or more salts of the alkaline earth metal or alkali metal and is selected from the group consisting of $K_2CO_3$, $KNO_3$, KCl, potassium acetate ($CH_3CO_2K$), potassium lactate ($CH_3CH(OH)CO_2K$), $Na_2CO_3$, $Li_2CO_3$ and $Rb_2CO_3$.

The reaction vessel/solution that is used in the process is heated to a temperature of less than 250° C. Preferably the vessel is heated to from 50° C. to 180° C., from 60° C. to 170° C., from 80° C. to 150° C.; more preferably from 60° C. to 140° c.

According to the process of the present invention the inventors have surprisingly found that the yield of the methionine α-hydroxy analogue and derivatives thereof is greater than than the yield of MVG. If a C4 saccharide is the substrate, the yield of MVG is less than 5%, 4%, 3%, 2%, 1%.

Also, the inventors have surprisingly found that the yield of the methionine α-hydroxy analogue and derivatives thereof prepared according to the process of the present invention is greater than 15%.

The process for the preparation of methionine α-hydroxy analogue and derivatives thereof may be carried out in a batch scale reaction or a continuous flow reaction.

The one or more sugars or derivatives thereof are contacted with the metallo-silicate composition in the presence of the compound comprising sulphur and the solvent in a reactor. Sugars or derivatives thereof are gradually converted into the methionine α-hydroxy analogue and derivatives thereof. Preferably the reactor is stirred such as by a mixer or by the flow through the reactor. The conversion is preferably carried out under heating and for a period of time sufficient to achieve a high conversion of the sugars and derivatives thereof. Preferably for a period of from 10 minutes to 12 hours, more preferred of from 20 to 300 minutes. The methionine α-hydroxy analogue and derivatives thereof may be recovered as it is or it may be purified such as by distillation.

Products obtained from bio materials such as sugars, will have a significantly higher content of $^{14}C$ carbon than the same products obtained from petrochemical sources. Previously, methionine and its derivatives for use as nutritional supplements have been obtained from fossil fuels.

Accordingly a product is provided according to the present invention, which is obtainable by the process for the preparation of a methionine α-hydroxy analogue and derivatives thereof from sugars described above. Such a product is characteristic by having a $^{14}C$ content above 0.5 parts per trillion of the total carbon content. The methionine α-hydroxy analogue and derivatives thereof may be 2-hydroxy-4-(methylthio)butanoic acid, salts and esters thereof and at least 70% of the initial carbon may be recovered in that form.

LEGENDS TO THE FIGURES

FIG. 1. Yield of methyl ester of methionine α-hydroxy analogue (2-hydroxy-4-(methylthio)butanoic acid methyl ester) with Sn-Beta as catalyst using glycolaldehyde as sugar in continuous flow reaction. Feed composition: 9 g/L glycolaldehyde in methanol as solvent, 10.7 wt % of water, 0.9 g/L methanethiol.

Figure 2:
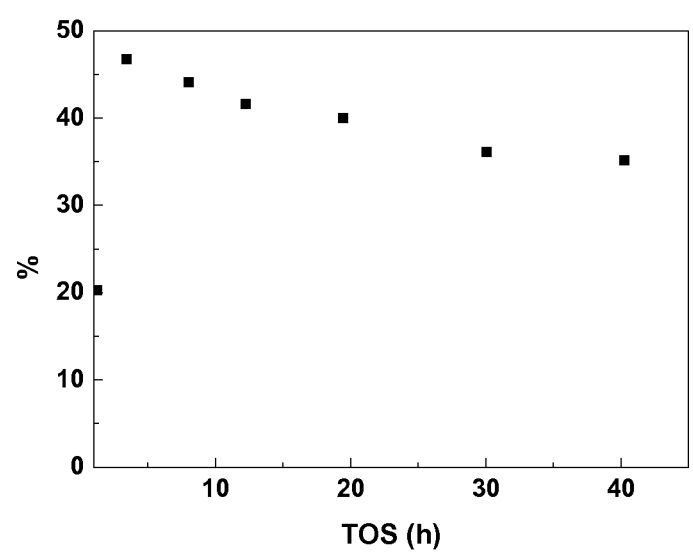

FIG. 2. Yield of methyl ester of methionine α-hydroxy analogue (2-hydroxy-4-(methylthio)butanoic acid methyl ester) with Sn-Beta as catalyst using glycolaldehyde in the presence of $C_1$-$C_3$ oxygenate compounds in continuous flow reaction. Feed composition: 10.9 g/L glycolaldehyde in methanol as solvent, 8 wt % of water, 0.7 g/L methanethiol.

EXAMPLES

Preparation of Catalyst

Sn-BEA (Si/Sn=125) is prepared according to a modification of the procedure described in U.S. Pat. No. 4,933,161. Commercial zeolite Beta (Zeolyst, Si/Al 12.5, ammonium form) is calcined (550° C. for 6 h) to obtain the H form (de-aluminated form) and treated with 10 grams of concentrated nitric acid (Sigma-Aldrich, 65%) per gram of zeolite beta powder for 12 h at 80° C. The resulting solid is filtered, washed with ample water and calcined (550° C. for 6 h) to obtain the de-aluminated Beta. This solid is impregnated by incipient wetness methodology with a Sn/Si ratio of 125. For this purpose, tin (II) chloride (0.128 g, Sigma-Aldrich, 98%) is dissolved in water (5.75 mL) and added to the de-aluminated Beta (5 g). After the impregnation process, the samples are dried 12 h at 110° C. and calcined again (550° C. for 6 h)

Example 1

Catalytic Reaction in Batch Reaction

A stainless steel pressure vessel (40 cc, Swagelok) is charged with 15.0 g of methanol (Sigma-Aldrich, >99.8%), 0.450 g of sucrose (Fluka, >99.0%) and 0.150 g of catalyst. The reactor is then filled with 75 mL of methanethiol at 1.7 bar, pressurized at 11 bar with $N_2$ and closed. The reactor is heated in an oil bath at 170° C. under stirring (700 rpm). The reaction is continued for the desired time and after this period, the reaction is quenched by submerging the vessel in cold water. Samples from the reaction vessel are filtered and analysed by HPLC (Agilent 1200, Biorad Aminex HPX-87H column at 65° C., 0.05 M $H_2SO_4$, 0.6 ml min$^{-1}$) to quantify unconverted hexoses and dihydroxyacetone (DHA), glyceraldehyde (GLA); and GC (Agilent 7890 with a Phenomenex Solgelwax column) was used to quantity: methyl lactate (ML), methyl vinylglycolate (MVG, methyl 2-hydroxy-3-butenoate), glycolaldehyde dimethylacetal (GADMA) and MHA (Methionine α-hydroxy analogue and derivatives thereof).

The methionine α-hydroxy analogue esters prepared according to Example 1 may be reacted in a basic aqueous solution, such as aqueous NaOH or KOH or an acidic aqueous solution, such as aqueous HCl, or solid acid catalyst to produce the salts and the acid derivatives of the methionine α-hydroxy analogue ester.

TABLE 1

Conversion of sugars to methionine α-hydroxy analogue and derivatives thereof in the Presence of a Metallosilicate composition and sulfur compound. MHA means methionine α-hydroxy analogue and derivatives thereof. In the case of solvents A, B and C, MHA means 2-hydroxy-4-(methylthio)butanoic acid methyl ester. In the case of H2O as solvent, MHA means 2-hydroxy-4-(methylthio)butanoic acid. In the case of IPA, MHA means 2-hydroxy-4-(methylthio)butanoic acid isopropyl ester. In the case of ethanol, MHA means 2-hydroxy-4-(methylthio)butanoic acid ethyl ester.

| Ex | Sugar | Catalyst | Solvent | CH3SH/mL | MHA Yield | MVG Yield | Conversion | Temp | Time |
|---|---|---|---|---|---|---|---|---|---|
| 1 | Erythrulose | Sn-BEA | A | 25 | 20.7 | 0 | 68.1 | 60 | 16 |
| 2 | Erythrulose | Sn-BEA | A | 25 | 6.8 | 0 | 43.8 | 60 | 4 |
| 3 | Erythrulose | Sn-BEA | A | 50 | 3.5 | 0 | 14.0 | 60 | 4 |
| 4 | Erythrulose | Sn-BEA | A | 25 | 24.3 | 0 | 77.7 | 100 | 4 |

TABLE 1-continued

Conversion of sugars to methionine α-hydroxy analogue and derivatives thereof in the Presence of a Metallosilicate composition and sulfur compound. MHA means methionine α-hydroxy analogue and derivatives thereof. In the case of solvents A, B and C, MHA means 2-hydroxy-4-(methylthio)butanoic acid methyl ester. In the case of H2O as solvent, MHA means 2-hydroxy-4-(methylthio)butanoic acid. In the case of IPA, MHA means 2-hydroxy-4-(methylthio)butanoic acid isopropyl ester. In the case of ethanol, MHA means 2-hydroxy-4-(methylthio)butanoic acid ethyl ester.

| Ex | Sugar | Catalyst | Solvent | CH3SH/mL | MHA Yield | MVG Yield | Conversion | Temp | Time |
|---|---|---|---|---|---|---|---|---|---|
| 5 | Erythrulose | Sn-BEA | A | 25 | 11.4 | 0 | 86.6 | 60 | 4 |
| 6 | Erythrulose | Sn-BEA | A | 25 | 12.7 | 17.4 | 93.8 | 170 | 16 |
| 7 | Erythrulose | Sn-MFI | A | 25 | 29.1 | 0 | 81.3 | 100 | 4 |
| 8 | Erythrulose | Sn-FAU | A | 25 | 0 | 0 | 54.0 | 100 | 4 |
| 9 | Erythrulose | Sn-MOR | A | 25 | 0 | — | 97.2 | 100 | 4 |
| 10 | Erythrulose | Sn-BEA | IPA | 25 | 0 | 0 | 66.7 | 100 | 4 |
| 11 | Erythrulose | Sn-BEA | EtOH | 25 | 15.6 | 0 | 68.7 | 100 | 4 |
| 12 | Erythrulose | Sn-BEA | H2O | 25 | 0 | 0 | 0 | 80 | 4 |
| 13 | Erythrulose | Sn-BEA | A | 25 | 21.2 | 0 | 76.6 | 140 | 4 |
| 14 | Erythrulose | Sn-BEA | A | 50 | 19.7 | 8.3 | 85.7 | 170 | 4 |
| 15 | Erythrulose | Sn-BEA | A | 25 | 6.7 | 0 | 27.4 | 60 | 4 |
| 16 | Erythrulose | Sn-BEA | A | 25 | 14.8 | 0 | 84.6 | 170 | 4 |
| 17 | Erythrulose | Sn-BEA | B | 25 | 23.7 | 0 | 73.0 | 100 | 4 |
| 18 | Erythrulose | Sn-BEA | C | 25 | 22.1 | 0 | 76.9 | 100 | 4 |
| 19 | Glucose | Sn-BEA | A | 25 | 3.6 | <<1 | 0 | 160 | 3 |
| 20 | Glucose | Sn-BEA | A | 25 | 8.3 | 0 | 100 | 160 | 4 |
| 21 | Glucose | Sn-BEA | A | 25 | 5.0 | 5.8 | 96.8 | 170 | 16 |
| 22 | GA | Sn-BEA | A | 25 | 12.7 | 0 | 44.3 | 120 | 4 |
| 23 | GA | Sn-BEA | A | 25 | 17.4 | 0 | 41.9 | 120 | 16 |
| 24 | GA | Sn-BEA | A | 25 | 14.9 | 5.4 | 30.7 | 140 | 16 |
| 25 | GA | Sn-BEA | A | 10 | 7.5 | 0 | 48.0 | 60 | 4 |
| 26 | GA | Sn-BEA | A | 25 | 5.0 | 0 | 8.4 | 60 | 4 |
| 27 | GA | Sn-BEA | A | 25 | 17.7 | 4 | 28.9 | 60 | 3 |
| 28 | GA | Sn-BEA | H2O | 25 | 0 | 0 | 51.3 | 80 | 4 |
| 29 | GA | Sn-BEA | A | 25 | 0 | 0 | 39.4 | 60 | 4 |
| 30 | GA | Sn-BEA | A | 25 | 0 | 0 | 52.3 | 60 | 4 |
| 31 | GA | Sn-BEA | A | 10 | 0 | 0 | 51.1 | 60 | 4 |
| 32 | GA | Sn-BEA | B | 25 | 0 | 0 | 46.5 | 60 | 4 |
| 33 | GA | Sn-BEA | C | 25 | 5.0 | 0 | 88.9 | 120 | 4 |
| 34 | GA | Sn-BEA | A | 25 | 8.3 | 0 | 62.1 | 120 | 4 |
| 35 | Sucrose | Sn-BEA | A | 25 | 2.0 | 4.2 | 96 | 170 | 16 |
| 36 | Sucrose | Sn-BEA | A | 25 | 0.9 | 0 | 72.8 | 160 | 3 |
| 37 | MVG | Sn-BEA | A | 25 | 0 | | 0 | 100 | 4 |
| 38 | MVG | Sn-BEA | A | 25 | 0 | | 100 | 100 | 4 |
| 39 | MVG | Sn-BEA | A | 25 | 0.2 | | 12.7 | 170 | 16 |
| 40 | Erythrose | Sn-BEA | A | 25 | 0 | 0 | 0 | 60 | 4 |
| 41 | Erythrose | Sn-BEA | A | 25 | 20.0 | 0 | 80.0 | 100 | 4 |
| 42 | Erythrose | Sn-BEA | A | 25 | 19.3 | 0 | 94.0 | 170 | 4 |
| 43 | GA | Sn-BEA | A | 25 | 14.5 | 0 | 73.0 | 100 | 16 |
| 44 | GA | Sn-BEA & Amberlyst | A | 25 | 15.4 | 0 | 90.1 | 100 | 16 |
| 45 | Glucose | Sn-BEA | A | 85 | 8.3 | — | 79.4 | 120 | 4 |
| 46 | Erythrulose | Sn-BEA | A | 85 | 17.0 | — | 81.8 | 120 | 4 |

Solvent A: MeOH + 0.13 mmol K2CO3
Solvent B: MeOH + 0.06 mmol K2CO3
Solvent C: MeOH + 0.3 mmol K2CO3
GA = glycolaldehyde As observed in Table 1, C4 and C2 sugars (erythrulose and glycolaldehyde) provided the highest yields of methionine α-hydroxy analogue and derivatives thereof. Methanol and ethanol provided similar yields of the corresponding esters.

Example 2

Catalytic Reaction in Continuous Flow Reaction

Compositions comprising glycolaldehyde in the presence of $C_1$-$C_3$ oxygenate compounds may be prepared by pyrolysis of biomass or $C_5$-$C_6$ sugars such as glucose, sucrose, fructose or xylose. Exemplary pyrolysis reactions are provided in U.S. Pat. No. 7,094,932 B2 and PCT/EP2014/053587.

A composition comprising glycolaldehyde or $C_1$-$C_3$ oxygenate compounds with 814 g/L glycolaldehyde was dissolved in methanol (Sigma-Aldrich, 99.9%) at room temperature to reach a concentration of 10.9 g/l. Additionally, methanethiol (Sigma, 1.7 bar) and if necessary water, were added to the feed solution. Catalyst Sn-Beta (Si:Sn 125) prepared according to the above preparation was fractionized (0.25 g, 300-600 μm.) and loaded into a stainless steel 0.25 inch reactor. Glass wool was used to hold the catalyst in place. The reactor was introduced into an oven and the temperature of the reactor increased to 160° C. When the temperature was over 140° C., the pump was started with a flow of 0.05 ml/min.

As observed from FIGS. 1 and 2, stable yields of 2-hydroxy-4-(methylthio)butanoic acid methyl ester (over 30%) were obtained from glycolaldehyde in water and methanol using Sn-Beta as catalyst. The presence of other C1-C3 oxygentes (FIG. 2) did not affect the reaction of production of the methionine α-hydroxy analogue methyl ester.

Embodiments

The Present Invention may also be Described According to the Following Embodiments:

Embodiment 1. A process for the preparation of methionine α-hydroxy analogues comprising contacting one or more sugars or derivatives thereof with a metallosilicate composition in the presence of a compound comprising sulphur and a solvent.

Embodiment 2. The process according to embodiment 1, wherein the compound comprising sulphur is selected from the group consisting of $C_1$-$C_5$ alkyl thiol, $C_1$-$C_5$ alkyl thiol salt, dimethylmercaptan, dimethyl disulphide and hydrogen sulphide.

Embodiment 3. The process according to any one of embodiments 1 and 2, wherein the compound comprising sulphur is selected from the group consisting of methane thiol, dimethylmercaptan, dimethyl disulphide and hydrogen sulphide.

Embodiment 4. A process according to any one of embodiments 1 to 3, wherein the one or more sugars or derivatives thereof is selected from the group consisting of glucose, fructose, galactose, mannose, sucrose, xylose, erythrose, erythrulose, threose, glycolaldehyde and 2-hydroxy-γ-butyrolactone.

Embodiment 5. A process according to any one of embodiments 1 to 3, wherein the one or more sugars or derivatives thereof are derivatives obtained by subjecting one or more sugars selected from the group consisting of glucose, fructose, galactose, mannose, sucrose, xylose, erythrose, erythrulose, threose; to a pyrolysis step to obtain a pyrolysis product and subsequently contacting the pyrolysis product with the metallo-silicate composition in the presence of the compound comprising sulphur and the solvent Embodiment 6. The process according to any one of embodiments 1 to 5, wherein the metallo-silicate composition is a zeotype material.

Embodiment 7. The process according to embodiment 6, wherein the zeotype material is one or more materials selected from the group consisting of Sn-BEA, Sn-MFI, Sn-FAU, Sn-MCM-41 and Sn-SBA-15.

Embodiment 8. The process according to any one of embodiments 1 to 7, wherein the solvent is selected from one or more of the group consisting of methanol, ethanol, 1-propanol, 1-butanol, 2-propanol, 2-butanol, DMSO and water.

Embodiment 9. The process according to any one of embodiments 1 to 8, wherein the methionine α-hydroxy analogues is selected from the group consisting of 2-hydroxy-4-(methylthio)butanoic acid, salts and esters thereof.

Embodiment 10. The process according to any one of embodiments 1 to 9, wherein the methionine α-hydroxy analogues is selected from the group consisting of 2-hydroxy-4-(methylthio)butanoic acid, 2-hydroxy-4-(methylthio)butanoic acid methyl ester and 2-hydroxy-4-(methylthio)butanoic acid ethyl ester Embodiment 11. The process according to any one of embodiments 1 to 10, wherein the temperature of the process is less than 200° C., preferably within the range of from 50 to 200° C.

Embodiment 12. The process according to any one of embodiments 1 to 11, wherein the reaction solution comprises one or more basic components selected from the group consisting of a metal salt and a polymer resin.

Embodiment 13. The process according to any one of embodiments 1 to 12, wherein the yield of the methionine α-hydroxy analogues is greater than methyl vinylglycolate (MVG).

Embodiment 14. The process according to any one of embodiments 1 to 13, wherein the yield of the methionine α-hydroxy analogues is greater than 15%.

Embodiment 15. The process according to any one of embodiments 1 to 14, wherein the process is a continuous process.

Embodiment 16. The process according to any one of embodiments 1 to 15, wherein the methionine α-hydroxy analogues are purified by distillation.

Embodiment 17. The process according to embodiment 9, wherein the 2-hydroxy-4-(methylthio)butanoic esters are hydrolysed.

Embodiment 18. Use of 2-hydroxy-4-(methylthio)butanoic acid, salts and esters thereof prepared by the process of claims 9 to 17 for a nutritional supplement.

The invention claimed is:

1. A process for the preparation of a methionine α-hydroxy analogue and derivatives thereof of the formula:

$$R'-S-CH_2-CH_2-CHOH-COO-R \qquad (I)$$

wherein R is selected from the group consisting of H, $C_1$-$C_8$ alkyl, alkaline or alkaline-earth metals; and R' is selected from the group consisting of H and methyl; and
wherein the process comprises a step of contacting one or more sugars or derivatives thereof selected from the group consisting of glucose, fructose, galactose, mannose, sucrose, xylose, erythrose, erythrulose, threose, glycolaldehyde, methyl vinyl glycolate,vinyl glycolic acid and 2-hydroxyl-α-butyrolactone with a metallosilicate zeotype material, in the presence of a compound comprising sulphur and a solvent, wherein the metallo-silicate zeotype material has a framework structure selected from the group consisting of BEA, MFI, FAU, MOR, and FER, with a metal and/or metal oxide component.

2. A process according to claim 1, wherein the compound comprising sulphur is selected from the group consisting of $C_1$-$C_5$ alkyl thiol, $C_1$-$C_5$ alkyl thiol salt, dimethylmercaptan, dimethyl disulphide and hydrogen sulphide.

3. A process according to claim 2, wherein the compound comprising sulphur is selected from the group consisting of methane thiol, methanethiolate alkaline salts, dimethylmercaptan, dimethyl disulphide, and hydrogen sulphide.

4. A process according to claim 1, wherein the one or more sugars or derivatives thereof subjected to a pyrolysis step to obtain a pyrolysis product and subsequently the pyrolysis product is contacted with the metallo-silicate zeotype material in the presence of the compound comprising sulphur and the solvent.

5. The process according to claim 1, wherein the zeotype material is one or more materials selected from the group consisting of Sn-BEA, Sn-MFI, Sn-FAU, Sn-MCM-41 and Sn-SBA-15.

6. The process according to claim 1, wherein the solvent is selected from one or more of the group consisting of methanol, ethanol, 1-propanol, 1-butanol, 2-propanol, 2-butanol, DMSO and water.

7. The process according to claim 1, wherein the methionine α-hydroxy analogue and derivatives thereof are selected from the group consisting of 2-hydroxy-4-(methylthio)butanoic acid, salts and esters thereof.

8. The process according to claim 1, wherein the methionine α-hydroxy analogue and derivatives thereof are selected from the group consisting of 2-hydroxy-4-(methylthio)butanoic acid, 2-hydroxy-4-(methylthio)butanoic acid methyl ester and 2-hydroxy-4-(methylthio)butanoic acid ethyl ester.

9. The process according to claim 1, wherein the contacting step is performed under heating.

10. The process according to claim 9, wherein the heating temperature is between 50 and 200° C.

11. The process according to claim 9, wherein the heating is continued for a period of from 10 minutes to 12 hours.

12. The process according to claim 1, further comprising performing the contacting step in the presence of one or more basic components selected from the group consisting of a metal salt and polymer resin.

13. The process according to claim 1, wherein the yield of the methionine α-hydroxy analogue and derivatives thereof are greater than the yield of methyl vinylglycolate (MVG).

14. The process according to claim 1, wherein the process is a continuous process.

15. The process according to claim 14, wherein the yield of the methionine α-hydroxy analogue and derivatives thereof is greater than 15%.

16. The process according to claim 14, wherein the weight hourly space velocity is between 0.005 and 10 h⁻¹, preferably between 0.1 and 1 h⁻¹.

17. The process according to claim 1, wherein the methionine α-hydroxy analogue and derivatives thereof are recovered.

18. The process according to claim 1, wherein the methionine α-hydroxy analogue and derivatives thereof are recovered by purification.

19. The process according to claim 1, wherein the methionine α-hydroxy analogue and derivatives thereof are purified by distillation.

20. The process according to claim 7, wherein the 2-hydroxy-4-(methylthio)butanoic esters are hydrolysed.

21. A process according to claim 1, wherein the zeotype material includes Sn which at least partially replaces aluminium in the material.

22. A process for the continuous preparation of a methionine α-hydroxy of the formula:

$$R'-S-CH_2-CH_2-CHOH-COO-R \quad (I)$$

wherein R is selected from the group consisting of H, $C_1$-$C_8$ alkyl, alkaline or alkaline-earth metals; and R' is selected from the group consisting of H and methyl; and wherein the process comprises a step of contacting one or more sugars or derivatives thereof selected from the group consisting of glucose, fructose, galactose, mannose, sucrose, xylose, erythrose, erythrulose, threose, glycolaldehyde, methyl vinyl glycolate, vinyl glycolic acid and 2-hydroxy-α-butyrolactone with a Sn-zeotype material comprising a BEA, MFI, FAU, MOR and FER framework structure, in the presence of a compound comprising sulphur and an alcoholic solvent selected from the group consisting of methanol, ethanol, 1-propanol, 1-butanol, 2-propanol and 2-butanol.

23. A process for the continuous preparation of a methionine α-hydroxy of the formula:

$$R'-S-CH_2-CH_2-CHOH-COO-R \quad (I)$$

wherein R is selected from the group consisting of H, $C_1$-$C_8$ alkyl, alkaline or alkaline-earth metals; and R' is selected from the group consisting of H and methyl; and wherein the process comprises contacting and heating one or more $C_2$-$C_6$ sugars or $C_2$-$C_6$ sugar derivatives with (1) a metal/ metal oxide containing zeolite material, (2) a compound comprising sulphur, and (3) an alcoholic solvent selected from one of methanol, ethanol, 1-propanol, 1-butanol, 2-propanol and 2-butanol, wherein the zeolite comprises a BEA, MFI, FAU, MOR or FER structure.

* * * * *